(12) United States Patent
Rao et al.

(10) Patent No.: US 9,259,588 B2
(45) Date of Patent: Feb. 16, 2016

(54) NEUROSTIMULATION PROGRAMMER AND METHOD FOR GLOBALLY ASSIGNING PARAMETER VALUES TO ELECTRODES

(71) Applicant: BOSTON SCIENTIFIC NEUROMODULATION CORPORATION, Valencia, CA (US)

(72) Inventors: Prakash Rao, Chicago, IL (US); Anita Yip, Los Angeles, CA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/042,266

(22) Filed: Sep. 30, 2013

(65) Prior Publication Data

US 2014/0100631 A1  Apr. 10, 2014

Related U.S. Application Data

(60) Provisional application No. 61/712,160, filed on Oct. 10, 2012.

(51) Int. Cl.
*A61N 1/08* (2006.01)
*A61N 1/372* (2006.01)
*A61N 1/36* (2006.01)

(52) U.S. Cl.
CPC ........ *A61N 1/37264* (2013.01); *A61N 1/36185* (2013.01); *A61N 1/37247* (2013.01)

(58) Field of Classification Search
CPC .................................................. A61N 1/37247
USPC ...................................................... 607/59, 60
See application file for complete search history.

(56) References Cited

U.S. PATENT DOCUMENTS

| 6,106,460 A | 8/2000 | Panescu et al. |
| 6,516,227 B1 | 2/2003 | Meadows et al. |
| 6,895,280 B2 | 5/2005 | Meadows et al. |
| 6,993,384 B2 | 1/2006 | Bradley et al. |
| 2004/0034394 A1 | 2/2004 | Woods et al. |

(Continued)

OTHER PUBLICATIONS

PCT International Search Report for PCT/US2013/062724, Applicant: Boston Scientific Neuromodulation Corporation, Form PCT/ISA/210 and 220, dated Dec. 13, 2013 (5pages).

(Continued)

*Primary Examiner* — Allen Porter, Jr.
(74) *Attorney, Agent, or Firm* — Schwegman Lundberg & Woessner, P.A.

(57) ABSTRACT

An external control device for use with a neurostimulator coupled to electrodes. The external control device comprises a user interface configured for receiving input from a user, and including a display screen configured for displaying graphical representations of the electrodes. The external control device further comprises a controller/processor configured for, in response to the input from the user, linking a subset of the electrodes together, and globally assigning at least one of the same stimulation amplitude value and same on/off state to each of the electrodes. The controller/processor may also be configured for, in response to the input from the user, assigning at least one stimulation parameter value to one of the electrodes, copying/cutting the at least one stimulation parameter value from the one electrode, and pasting the at least one stimulation parameter value to the other electrode and modifying current values of other electrodes to maintain 100% current.

20 Claims, 12 Drawing Sheets

(56) References Cited

U.S. PATENT DOCUMENTS

| | | | |
|---|---|---|---|
| 2006/0017749 | A1 | 1/2006 | McIntyre et al. |
| 2006/0259099 | A1* | 11/2006 | Goetz et al. .................. 607/66 |
| 2008/0154340 | A1* | 6/2008 | Goetz et al. .................. 607/59 |
| 2010/0010566 | A1 | 1/2010 | Thacker et al. |
| 2010/0121409 | A1 | 5/2010 | Kothandaraman et al. |
| 2011/0125214 | A1 | 5/2011 | Goetz et al. |
| 2011/0307032 | A1 | 12/2011 | Goetz et al. |
| 2012/0109230 | A1 | 5/2012 | Kothandaraman et al. |
| 2012/0239109 | A1 | 9/2012 | Lee |
| 2012/0239110 | A1 | 9/2012 | Lee et al. |
| 2012/0290041 | A1 | 11/2012 | Kim et al. |
| 2013/0131760 | A1 | 5/2013 | Rao et al. |
| 2013/0158628 | A1 | 6/2013 | Kothandaraman et al. |
| 2014/0100632 | A1* | 4/2014 | Rao et al. .................. 607/59 |

OTHER PUBLICATIONS

PCT Written Opinion of the International Search Authority for PCT/US2013/062724, Applicant: Boston Scientific Neuromodulation Corporation, Form PCT/ISA/237, dated Dec. 13, 2013 (7pages).

PCT International Search Report for PCT/US2013/062732, Applicant: Boston Scientific Neuromodulation Corporation, Form PCT/ISA/210 and 220, dated Dec. 10, 2013 (4pages).

PCT Written Opinion of the International Search Authority for PCT/US2013/062732, Applicant: Boston Scientific Neuromodulation Corporation, Form PCT/ISA/237, dated Dec. 10, 2013 (3pages).

File History of U.S. Appl. No. 61/452,965, Neurostimulation System for Defining a Generalized Ideal Multipole Configuration, Inventor: Dongchul Lee et al., filed Mar. 15, 2011.

File History of U.S. Appl. No. 61/486,141, Neurostimulation Sytem with On-Effector Programmer Control, Inventor: Chester Kim et al., filed May 13, 2011.

File History of U.S. Appl. No. 61/561,760, Technique for linking Electrodes Together During Programming of Neurostimulation System, Inventor: Prakash Rao et al., filed Nov. 18, 2011.

File History of U.S. Appl. No. 61/576,924, Seamless Integration of Different Programing Modes for a Neurostimulator Programming System, Inventor: Sridhar Kothandaraman et al., filed Dec. 16, 2011.

"U.S. Appl. No. PCT/US2013/062724, International Preliminary Report on Patentability mailed Apr. 23, 2015", 9 pgs.

* cited by examiner

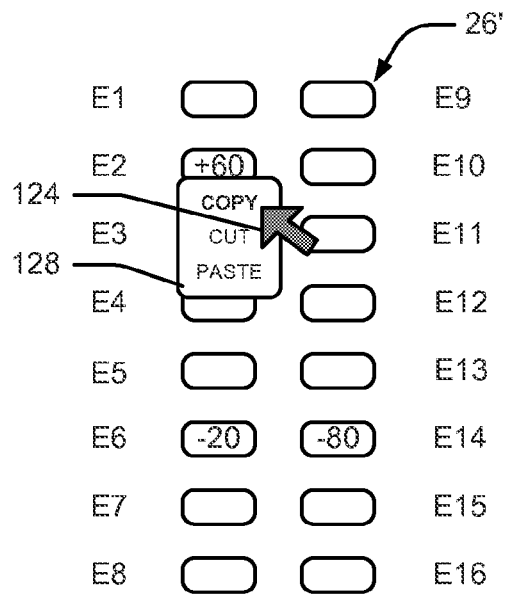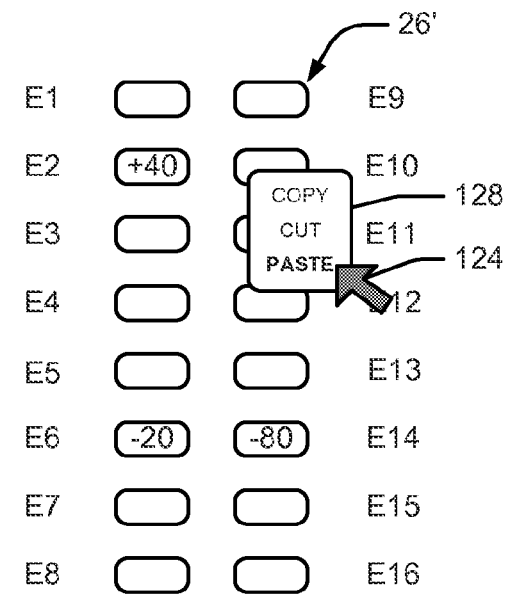
FIG. 11A    FIG. 11B
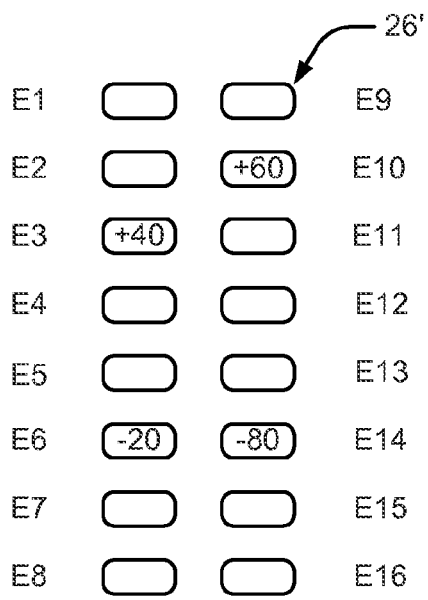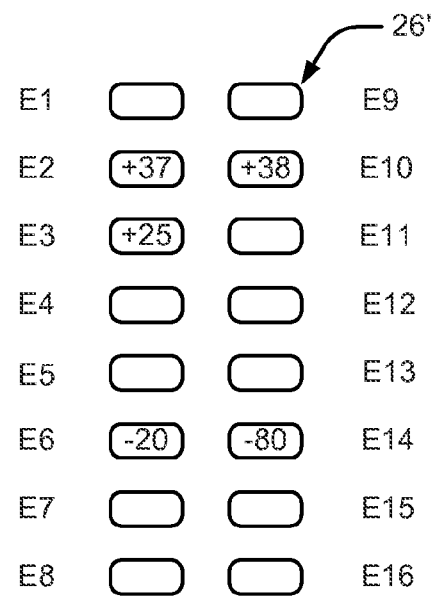
FIG. 11C    FIG. 11D

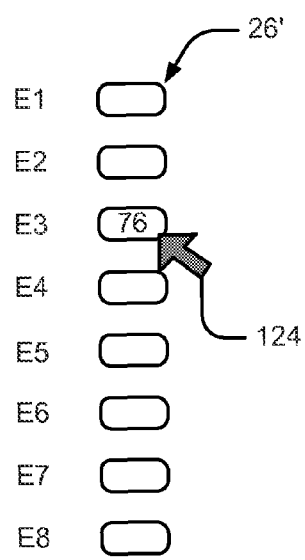 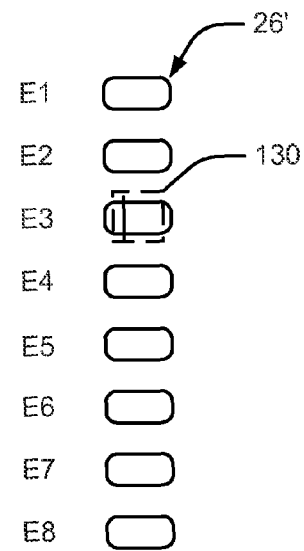 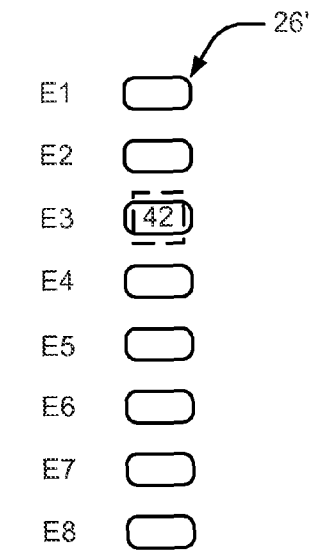
FIG. 12A    FIG. 12B    FIG. 12C
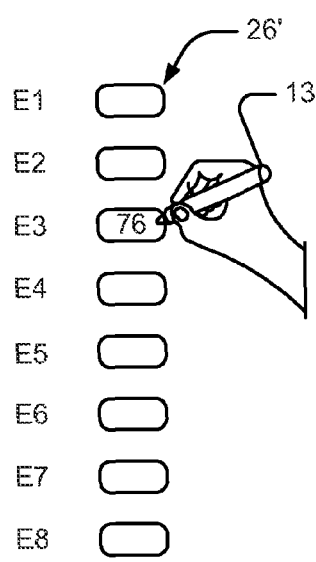 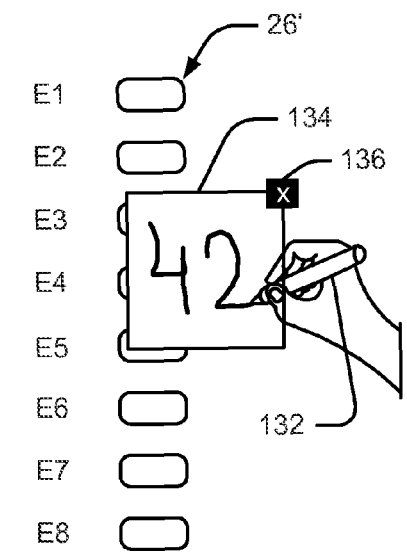 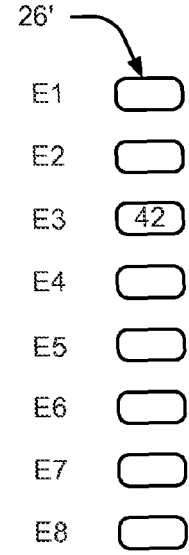
FIG. 13A    FIG. 13B    FIG. 13C

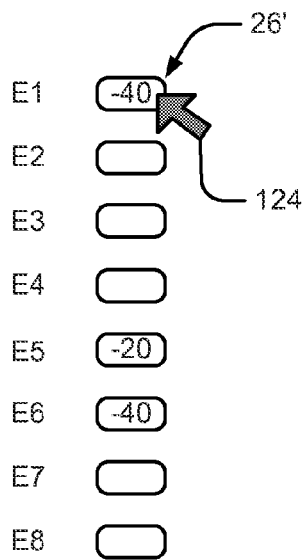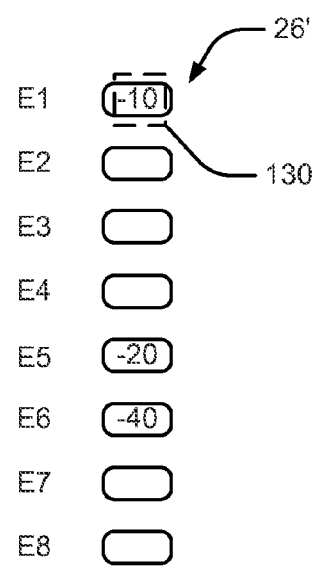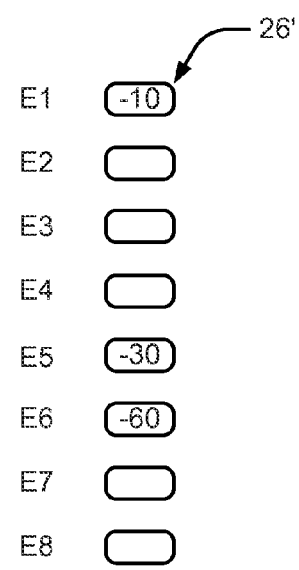
FIG. 14A    FIG. 14B    FIG. 14C
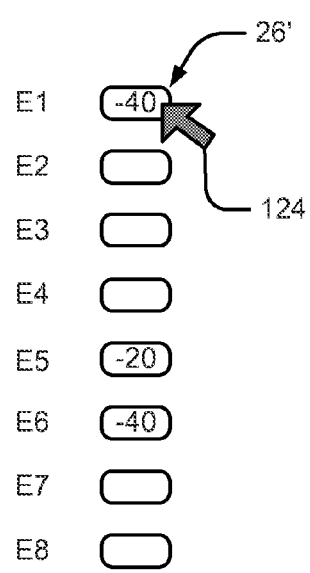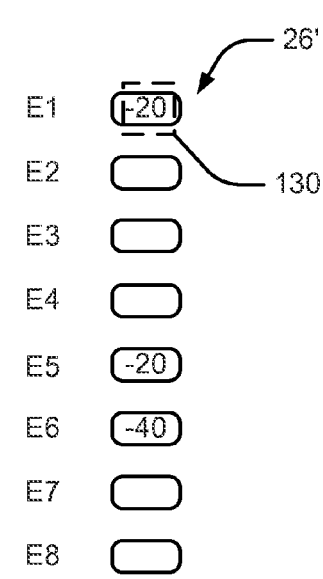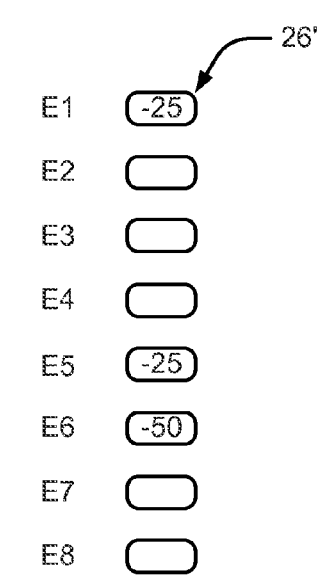
FIG. 15A    FIG. 15B    FIG. 15C

NEUROSTIMULATION PROGRAMMER AND METHOD FOR GLOBALLY ASSIGNING PARAMETER VALUES TO ELECTRODES

RELATED APPLICATION DATA

The present application claims the benefit under 35 U.S.C. §119 to U.S. provisional patent application Ser. No. 61/712,160, filed Oct. 10, 2012. The foregoing application is hereby incorporated by reference into the present application in its entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device in the form of a remote control to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, a remote control can be used to instruct the neurostimulator to generate electrical stimulation pulses in accordance with the selected stimulation parameters. Typically, the stimulation parameters programmed into the neurostimulator can be adjusted by manipulating controls on the remote control to modify the electrical stimulation provided by the neurostimulator system to the patient. Thus, in accordance with the stimulation parameters programmed by the remote control, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator, and optionally the remote control, with the optimum stimulation parameter set or sets.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an IPG. Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. Once a polarity and the amplitude (either as an absolute or a percentage) for the current or voltage on an active electrode is selected in a typical computerized programming system, the polarity and amplitude value may be displayed on a display screen in association with this electrode to the user.

Despite the fact that computerized programming systems have been used to speed up the programming process, programming of an electrical stimulation system using present-day computerized programming systems may still be a relatively time-consuming process. For example, when in a manual mode, the clinician must individually select stimulation parameters (such as the polarity and amplitude) for each active electrode. For adjusting the amplitude for each electrode, this is typically accomplished by repeatedly actuating a control to incrementally adjust the amplitude up or down (e.g., using an up arrow or down arrow). These incremental adjustments are convenient if the current amplitude value is close to the desired amplitude value. However, if the current and desired amplitude values are relatively far apart from each other, the control may have to be repeatedly actuated many times.

There, thus, remains a need to provide a more efficient means of manually programming the electrodes of a neurostimulation system.

SUMMARY OF THE INVENTION

In accordance with a first aspect of the present inventions, an external control device for use with a neurostimulator coupled to a plurality of electrodes is provided. The external control device is capable of conveying electrical stimulation energy into tissue in which the electrodes are implanted.

The external control device comprises a user interface configured for receiving input from a user, and including a display screen configured for displaying graphical representations of the electrodes. The external control device further comprises a controller/processor configured for, in response to the input from the user, linking a subset of the electrodes together, and globally assigning at least one of the same stimulation amplitude value (e.g., a fractionalized amplitude value) and same on/off state (which may include a polarization) to each of the electrodes of the electrode subset. The external control device further comprises output circuitry configured for transmitting the same stimulation amplitude value and/or same on/off state to the neurostimulator.

If the same stimulation amplitude value is assigned, the display screen may be configured for displaying an amplitude adjustment control, and the user input may comprise repeatedly actuating the amplitude adjustment control to incrementally increase or decrease the stimulation amplitude value of the electrode subset. Alternatively, the display screen may be configured for displaying a graphical data entry symbol, and the user input may comprise writing or typing the stimulation amplitude value into the graphical data entry symbol. If the same on/off state is assigned, the display screen may be configured for displaying an on/off state adjustment control, and the user input may comprise actuating the on/off adjustment control to change the on/off state of the electrode subset.

In one embodiment, the user input comprises using a pointing device. In one example, the user input comprises using the pointing device to draw a border that encompasses the graphical electrode representations corresponding to the electrode subset. In another example, the user input comprises using the pointing device to individually select the graphical electrode representations corresponding to the electrode subset. In an optional embodiment, the controller/processor is further configured for, in response to the input from the user, duplicating the same stimulation amplitude value and/or the same on/off state previously assigned to the electrodes of the electrode subset to electrodes of a different subset of electrodes. For example, the controller/processor may be configured for cutting/copying and pasting the same stimulation amplitude value and/or same on/off state previously assigned to the electrodes of the electrode subset to the electrodes of the different electrode subset. The external control device may comprise a housing containing the user interface, controller/processor, and output circuitry.

In accordance with a second aspect of the present inventions, another external control device for use with a neurostimulator coupled to a plurality of electrodes is provided. The other external control device is capable of conveying electrical stimulation energy into tissue in which the electrodes are implanted.

The other external control device comprises a user interface configured for receiving input from a user, and including a display screen configured for displaying graphical representations of the electrodes. The other external control device further comprises a controller/processor configured for, in response to the input from the user, assigning at least one stimulation parameter value to one of the electrodes, copying/cutting the stimulation parameter value(s) from the one electrode, and pasting the stimulation parameter value(s) to the other electrode. The other external control device further comprises output circuitry configured for transmitting the stimulation parameter value(s) to the neurostimulator.

In one embodiment, the stimulation parameter value(s) comprises at least one of a stimulation amplitude value (e.g., a fractionalized amplitude value) and an on/off state (which may include a polarization). If the same stimulation amplitude value is assigned, the display screen may be configured for displaying an amplitude adjustment control, and the user input may comprise repeatedly actuating the amplitude adjustment control to incrementally increase or decrease the stimulation amplitude value. Alternatively, the display screen may be configured for displaying a graphical data entry symbol, and the user input may comprise writing or typing the stimulation amplitude value into the graphical data entry symbol.

In one embodiment, the user input comprises using a pointing device, in which case, the controller/processor is configured for copying/cutting the stimulation amplitude value(s) from the one electrode in response to selecting the graphical electrode representation with the pointing device. In one example, the controller/processor is configured for pasting the stimulation parameter value(s) by dragging and dropping the graphical electrode representation into the other graphical electrode representation using the pointing device. In another example, the controller/processor is configured for pasting the stimulation parameter value(s) by dragging an edge of the graphical electrode representation using the pointing device to include a graphical representation of the other electrode. In still another example, the controller/processor is configured for copying/cutting the stimulation parameter value(s) in response to selecting the graphical electrode representation of the electrode with the pointing device to display a menu, and selecting a copy/cut command from the menu, and the stimulation parameter value(s) is pasted in response to pointing at the graphical electrode representation of the other electrode with the pointing device to display a menu, and selecting a paste command from the menu. The external control device may comprise a housing containing the user interface, controller/processor, and output circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained; a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 11A-11D are plan views respectively illustrating still another technique used by the CP of FIG. 6 to copy/cut and paste a stimulation parameter value from one electrode to another electrode;

FIGS. 12A-12C are plan views respectively illustrating one technique used by the CP of FIG. 6 to assign a new stimulation parameter value an electrode of the IPG;

FIGS. 13A-13C are plan views respectively illustrating another technique used by the CP of FIG. 6 to assign a new stimulation parameter value an electrode of the IPG;

FIGS. 14A-14C are plan views respectively illustrating one technique used by the CP of FIG. 6 to adjust stimulation parameter values of multiple electrodes of the IPG after assignment of a new value to an electrode; and FIGS. 15A-15C are plan views respectively illustrating another technique used by the CP of FIG. 6 to adjust stimulation parameter values of multiple electrodes of the IPG after assignment of a new value to an electrode.

DETAILED DESCRIPTION OF THE ILLUSTRATED EMBODIMENTS

The description that follows relates to spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
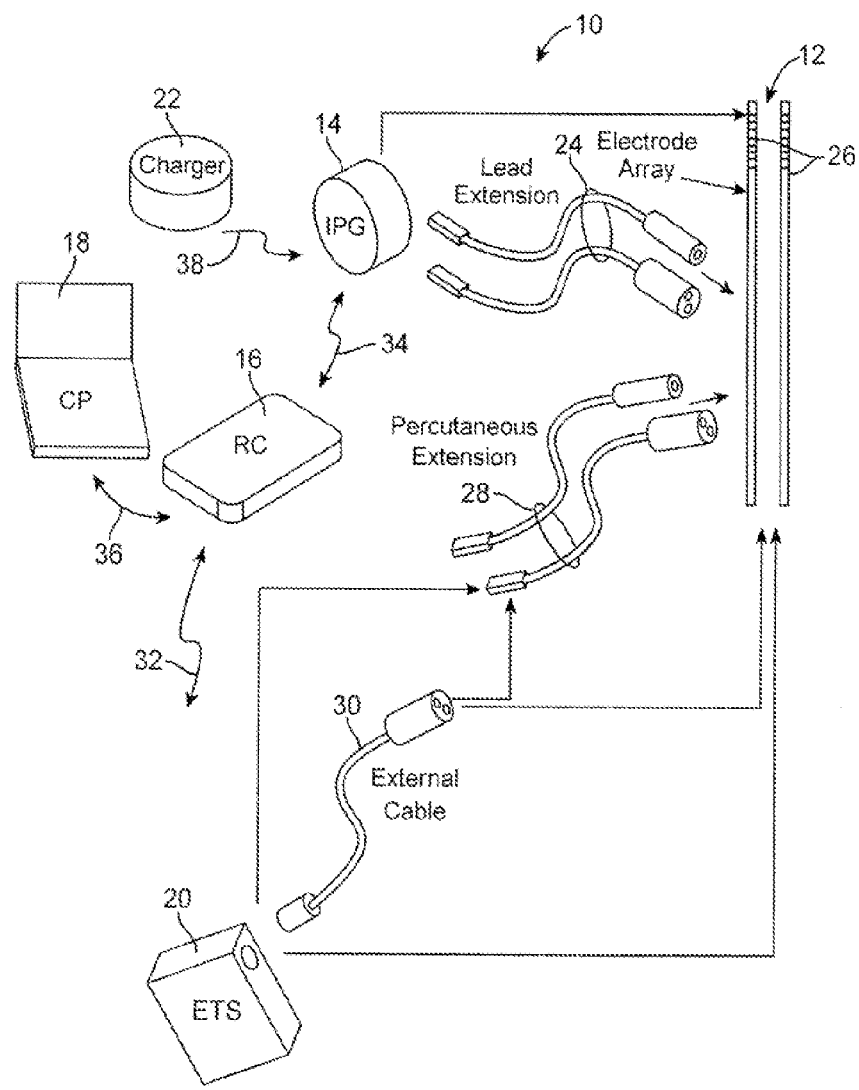
FIG. 1 is a plan view of a Spinal cord Stimulation (SCS) system constructed in accordance with one embodiment of the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. Alternatively, a surgical paddle lead can be used in place of or in addition to the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the IPG 14, ETS 20, and external charger 22 will not be described herein. Details of exemplary embodiments of these devices are disclosed in U.S. Pat. No. 6,895,280, which is expressly incorporated herein by reference.

Figure 2:
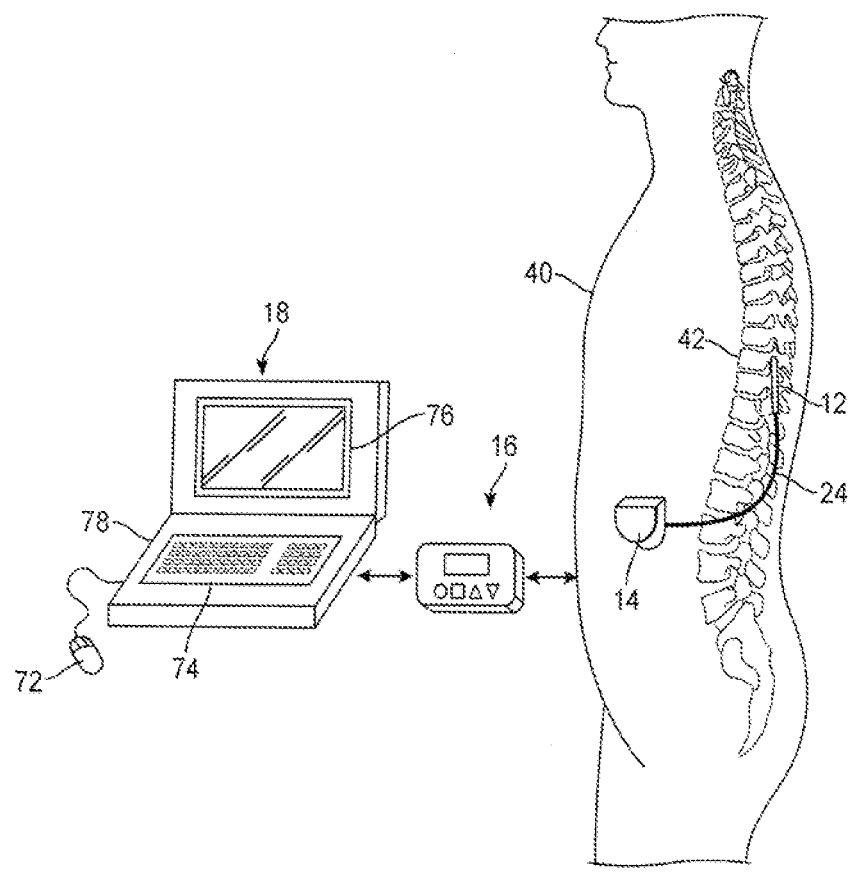
FIG. 2 is a perspective view of the arrangement of the SCS system of FIG. 1 with respect to a patient.

As shown in FIG. 2, the neurostimulation leads 12 are implanted within the spinal column 42 of a patient 40. The preferred placement of the neurostimulation leads 12 is adjacent, i.e., resting over, the spinal cord area to be stimulated. Due to the lack of space near the location where the neurostimulation leads 12 exits the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
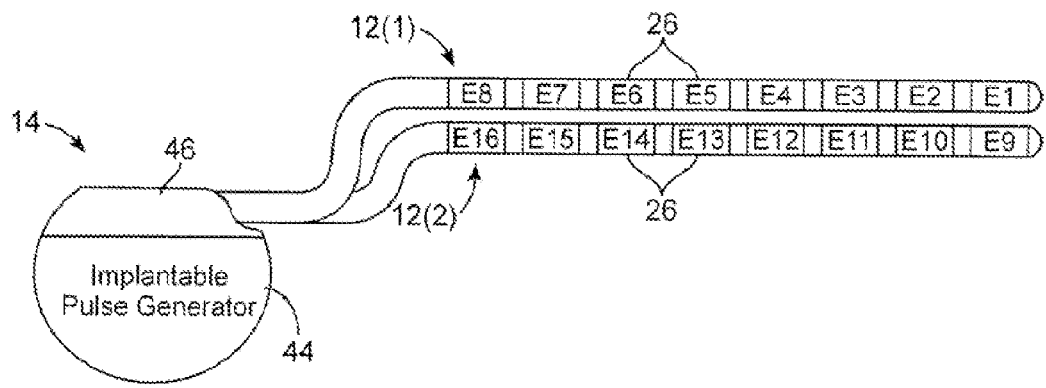
FIG. 3 is a profile view of an implantable pulse generator (IPG) and percutaneous leads used in the SCS system of FIG. 1.

Referring now to FIG. 3, the features of the neurostimulation leads 12 and the IPG 14 will be briefly described. One of the neurostimulation leads 12(1) has eight electrodes 26 (labeled E1-E8), and the other neurostimulation lead 12(2) has eight electrodes 26 (labeled E9-E16). The actual number and shape of leads and electrodes will, of course, vary according to the intended application. The IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (two ports 48 for two percutaneous leads) for receiving the proximal end(s) of the neurostimulation leads 12. In the case where the lead extensions 24 are used, the ports 48 may instead receive the proximal ends of such lead extensions 24.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, the IPG 14 can individually control the magnitude of electrical current flowing through each of the electrodes. In this case, it is preferred to have a current generator, wherein individual current-regulated amplitudes from independent current sources for each electrode 26 may be selectively generated. Although this system is optimal to take advantage of the invention, other stimulators that may be used with the invention include stimulators having voltage regulated outputs. While individually programmable electrode 26 amplitudes are optimal to achieve fine control, a single output source switched across electrodes 26 may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
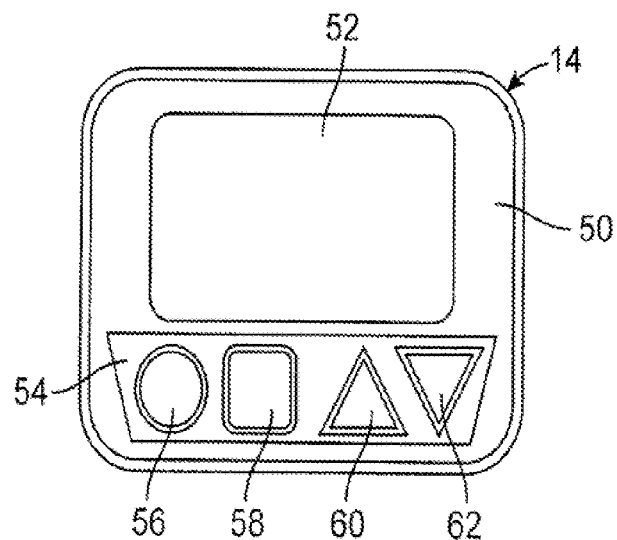
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons 60 can be provided for each stimulation parameter. Rather than using up/down buttons 60, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
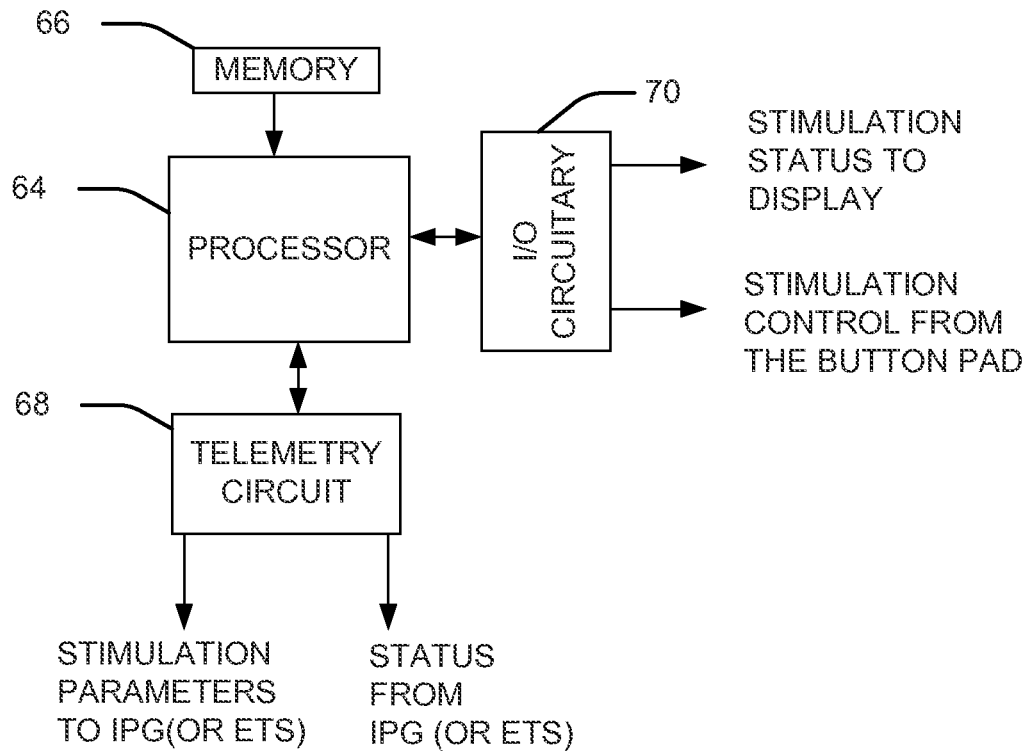
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory 66 of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 6:
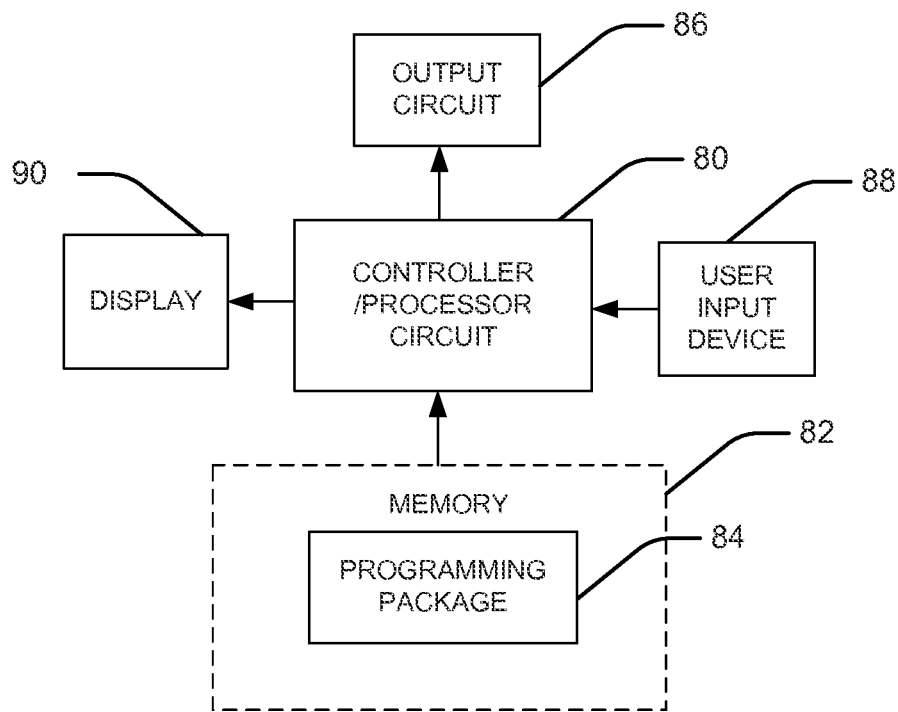
FIG. 6 is a block diagram of the internal components of a clinician's programmer (CP) used in the SCS system of FIG. 1.

To allow the user to perform these functions, the CP 18 includes a mouse 72, a keyboard 74, and a display screen 76 housed in a case 78. In the illustrated embodiment, the display screen 76 is a conventional screen. It is to be understood that in addition to, or in lieu of, the mouse 72, other directional programming devices may be used, such as a trackball, touchpad, or joystick, can be used. Alternatively, instead of being conventional, the display screen 76 may be a digitizer screen, such as touchscreen) (not shown), may be used in conjunction with an active or passive digitizer stylus/finger touch. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference. As shown in FIG. 6, the CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16. In addition, a user input device 88 such as a mouse or a keyboard is attached to provide user commands. Notably, while the controller/processor 80 is shown in FIG. 6 as a single device, the processing functions and controlling functions can be performed by a separate controller and processor 64. Thus, it can be appreciated that the controlling functions described below as being performed by the CP 18 can be performed by a controller, and the processing functions described below as being performed by the CP 18 can be performed by the processor 64.

Execution of the programming package 84 by the controller/processor 80 provides a multitude of programming screens that can be navigated through. These programming screens allow the clinician, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Figure 7:
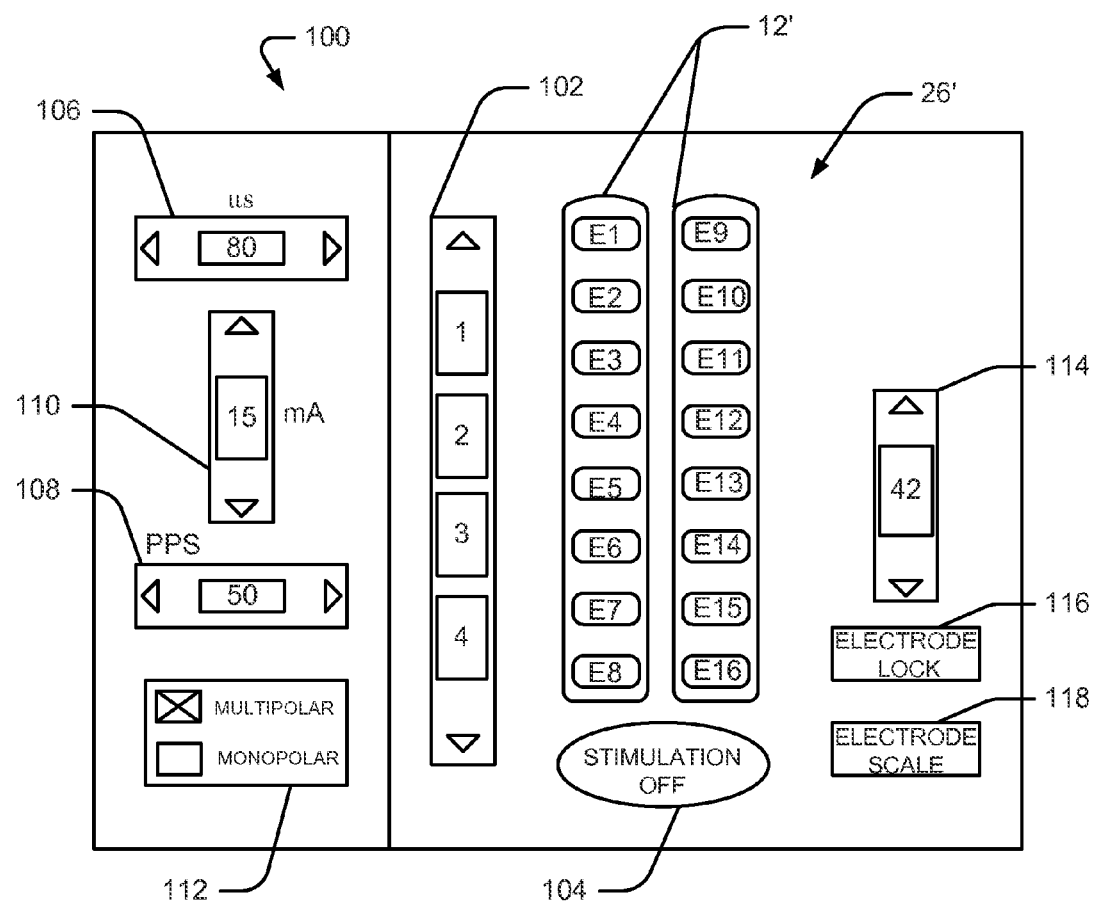
FIG. 7 is a plan view of a user interface of the CP of FIG. 6 for programming the IPG of FIG. 3.

As one example, and with reference to FIG. 7, an exemplary programming screen 100 generated by the CP 18 to allow a user to program the IPG 14 will now be described. The programming screen 100 includes various control elements described below that can be actuated to perform various control functions.

A pointing element may be used to graphically touch the control elements to perform the actuation event. As described above, in the case of a digitizer touch screen, the pointing element will be an actual pointing element (e.g., a finger or active or passive stylus) that can be used to physically tap the screen above the respective graphical control element or otherwise brought into proximity with respect to the graphical control element. In the case of a conventional screen, the pointing element will be a virtual pointing element (e.g., a cursor) that can be used to graphically click on the respective control element.

The programming screen 100 includes an electrode combination control 102 having arrows that can be actuated by the user to select one of four different electrode combinations 1-4. The programming screen 100 further includes stimulation on/off control 104 that can be alternately actuated initiate or cease the delivery of electrical stimulation energy from the IPG 14 via the selected electrode combination.

The programming screen 100 further includes various stimulation parameter controls that can be operated by the user to manually adjust stimulation parameters for the selected electrode combination. In particular, the programming screen 100 includes a pulse width adjustment control 106 (expressed in microseconds (µs)), a pulse rate adjustment control 108 (expressed in Hertz (Hz)), and a pulse amplitude adjustment control 110 (expressed in milliamperes (mA)). Each control includes a first arrow that can be actuated to decrease the value of the respective stimulation parameter and a second arrow that can be actuated to increase the value of the respective stimulation parameter.

Each of the electrode combinations 1-4 can be created using various control elements. In particular, the programming screen 100 displays graphical representations of the leads 12' including the electrodes 26'. In the illustrated embodiment, each electrode representation 26' takes the form of a closed geometric figure, and in this case a rectangle. In alternative embodiments, the electrode representations 26' can take the form of other types of closed geometric figures, such as circles. The electrode representations 26' can be touched with a physical pointing device or otherwise clicked with a virtual pointing device multiple times to switch the corresponding active electrode 26 between an on-state, which includes either positive polarity (anode) or a negative polarity (cathode), and an off-state. In essence, the electrode representations 26' themselves operate as the graphical control elements, the actuations of which prompt the controller/processor 80 to assign the polarities to the selected electrodes 26. In alternative embodiments, control elements separate from the electrode representations 26' may be used to change the polarity of the selected electrodes 26.

To enable selection between a multipolar configuration and a monopolar configuration, the programming screen 100 also includes multipolar/monopolar stimulation selection control 112, which includes check boxes that can be alternately actuated by the user to selectively provide multipolar or monopolar stimulation. If a multipolar electrode arrangement is desired, at least one of the electrodes E1-E16 will be selected as an anode (+) and at least one other of the electrodes E1-E16 will be selected as a cathode (−). If a monopolar electrode arrangement is desired, none of the electrodes E1-E16 will be selected as an anode (+), and thus, the electrode representations 26' can only be actuated to toggle the corresponding electrode 26 between a cathode (−) and off (0).

The programming screen 100 further includes an electrode specific current adjustment control 114 that can be manipulated to independently vary stimulation amplitude values for the electrodes E1-E16. In particular, for each electrode selected to be activated as either a cathode or anode, the clinician can click on the upper arrow of the control 114 to incrementally increase the absolute value of the stimulation amplitude of the selected electrode, and the clinician can click on the lower arrow of the control 114 to incrementally decrease the absolute value of the stimulation amplitude of the selected electrode. The control 114 also includes an indicator that provides an alphanumeric indication of the stimulation amplitude currently assigned to the selected electrode. In an optional embodiment, non-alphanumeric indicators, such as different colors, different color luminance, different patterns, different textures, different partially-filled objects, etc., can be used to indicate the stimulation amplitude currently assigned to the selected electrodes, as discussed in U.S. patent application Ser. No. 13/200,629, entitled "Neurostimulation System and Method for Graphically Displaying Electrode Stimulation Values," which is expressly incorporated herein by reference.

In the illustrated embodiments, the stimulation amplitude values are fractionalized electrical current values (% current), such that the values for each polarization totals to 100. However, in alternative embodiments, the stimulation amplitude values may be normalized current or voltage values (e.g., 1-10), absolute current or voltage values (e.g., mA or V), etc. Furthermore, the stimulation amplitude values may be parameters that are a function of current or voltage, such as charge (current amplitude×pulse width) or charge injected per second (current amplitude×pulse width×rate (or period)).

In alternative embodiments, a stimulation amplitude adjustment control (not shown) may appear next to the electrode representation 26' that has been touched or clicked, as described in U.S. patent application Ser. No. 13/200,629, which has been previously incorporated herein by reference, or may be superimposed over the electrode representation 26' that has been touched or clicked, as described in U.S. Provisional Patent Application Ser. No. 61/486,141, entitled "Neurostimulation System with On-Effector Programmer Control," which is expressly incorporated herein by reference. In another embodiment described in further detail later, the stimulation amplitude may be typed or written into a graphical data entry symbol associated with an electrode (e.g., next to or superimposed over the electrode representation 26').

In alternative embodiments, the programming screen 100 facilitates automated current steering; for example, by allowing the user to switch between a manual mode using the electrode selection and current adjustment techniques described above, an electronic trolling ("e-troll") mode that quickly sweeps the electrode array using a limited number of electrode configurations to gradually move a cathode in bipolar stimulation, and a Navigation programming mode that finely tunes and optimizes stimulation coverage for patient comfort using a wide number of electrode configurations, as described in U.S. Provisional Patent Application Ser. No. 61/576,924, entitled "Seamless Integration of Different Programming Modes for a Neurostimulator Programming System," which is expressly incorporated herein by reference. Virtual target poles may be utilized to steer the current within the electrode array, as described in U.S. Provisional Patent Application Ser. No. 61/452,965, entitled "Neurostimulation System for Defining a Generalized Virtual Multipole," which is expressly incorporated herein by reference.

More pertinent to the present inventions, the user interface of the CP 18 provides the user the ability to link a subset of the electrodes 26 together, and then globally assign the same value of a stimulation parameter to the electrode subset, such as, e.g., a stimulation amplitude value (and in this case, a fractionalized amplitude value) and/or an off/on state (which may include a polarization (positive and negative)). In particular, the user interface of the CP 18 is capable of displaying a programming screen that displays graphical representations of the electrodes and receives various inputs from the user. In response to these inputs, the controller/processor 80 links the subset of the electrodes 26 together and globally assigns the same stimulation parameter value to each of the electrodes 26 of the subset.

To this end, the programming screen 100 includes an electrode grouping control 116 that can be actuated (e.g., touched or clicked by the pointing device) to allow selected electrodes 26 to be linked together in a subset. In one embodiment, the actuation of the electrode grouping control 116 prompts the controller/processor 80 to display graphical control symbols, such as boxes, respectively adjacent the electrode representations 26'. These symbols can then be checked to prompt the controller/processor 80 to link electrodes corresponding to these checked symbols together, such that the electrodes 26 will be forced to have the same value of a stimulation parameter, and in this case, the same fractionalized amplitude value and on/off state. In alternative embodiments, the graphical symbols can take the form of closed geometric figures other than boxes, such as circles, stars, triangles, etc. With reference now to FIGS. 8A-8G, one example of linking selected electrodes 26 together in a subset and globally assigning the same on/off state and same stimulation amplitude value to each electrode 26 in the subset will be discussed.

Figure 8A:
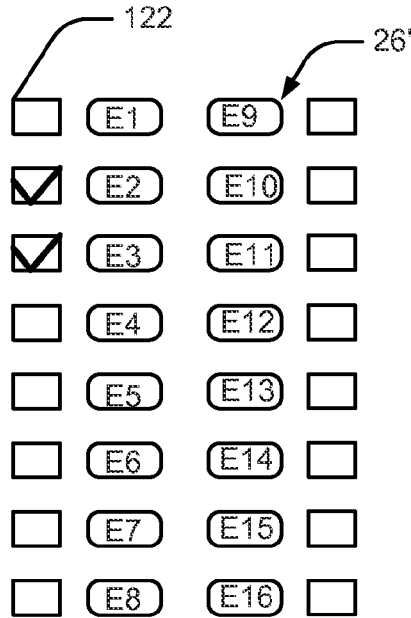
FIGS. 8A-8G are plan views respectively illustrating various techniques used by the CP of FIG. 6 to link selected electrodes together in a subset and globally assigning a stimulation parameter value to each electrode in the subset.
Figure 8B:
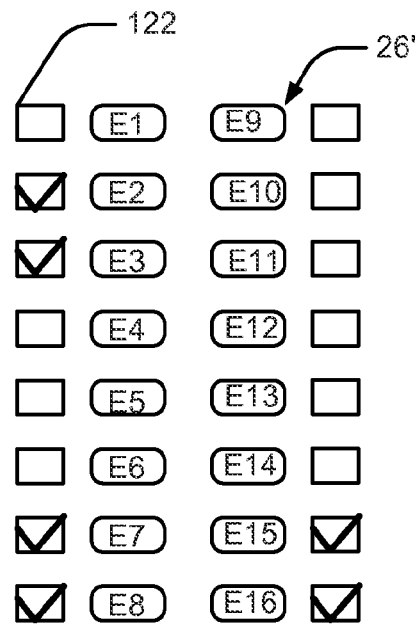
Figures 8C, 8D:
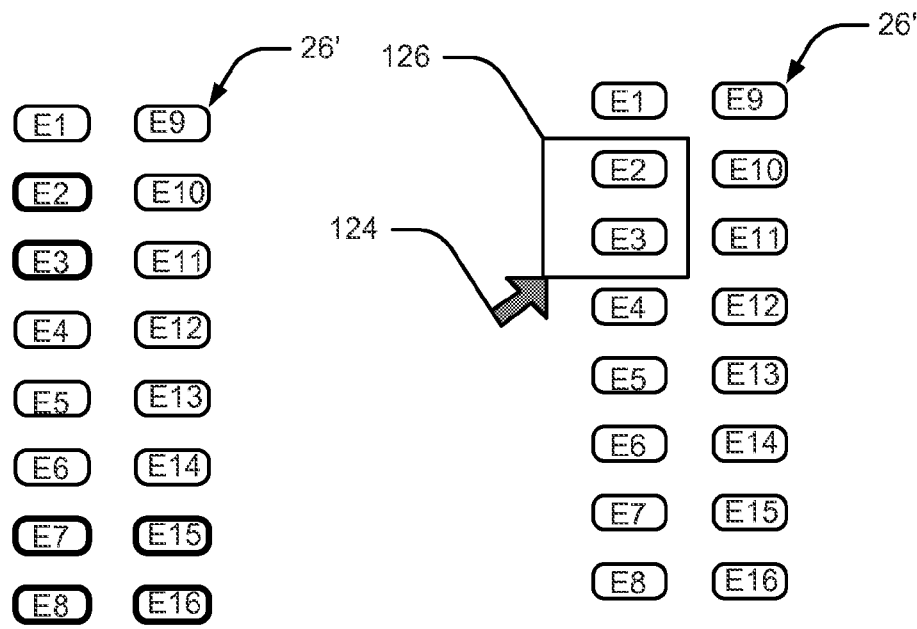

As illustrated in FIG. 8A, the electrode grouping control 116 (shown in FIG. 7) has been actuated to display the check boxes 120 adjacent all the electrode representations 26', with the check boxes 120 adjacent the electrode representations 26' associated with electrodes E2 and E3 being checked, indicating that electrodes E2 and E3 have been selected to be linked. The electrode grouping control 116 can be actuated again to actually link the electrodes 26 that have been selected to be linked, and in this case, electrodes E2 and E3 together. Any of the check boxes 120 adjacent the electrode representations 26' associated with remaining electrodes may be checked to create another electrode subset. For example, as shown in FIG. 8B, the check boxes 120 adjacent the electrode representations 26' associated with electrodes E7, E8, E15, and E16 have been checked, indicating that electrodes E7, E8, E15, and E16 have been selected to be linked. The electrode grouping control 116 can be actuated again to actually link the electrodes 26 that have been selected to be linked, and in this case, electrodes E7, E8, E15, and E16 together. As illustrated in FIG. 8C, the electrode grouping control 116 can be actuated yet again to remove the check boxes 120 from the display, and displaying indicators distinguishing the different electrode subsets (shown in bold in FIG. 8C). For example, the electrode representations 26' corresponding to the different electrode subsets may be displayed with different colors (e.g., blue for electrodes E2 and E3, and red for electrodes E7, E8, E15, and E16).

In an alternative embodiment, rather than using check boxes to link electrodes together, an actual or virtual pointing device 124 (in the illustrated case, a cursor) can be dragged across the display to draw a border 126 (e.g., a rectangle) around the graphical electrode representations 26' corresponding to the electrodes 26 to be linked (in the exemplary case, electrodes E2 and E3), as shown in FIG. 8D. This is especially an efficient technique to employ when the electrodes 26 to be linked are all immediately adjacent to each other. More alternatively, a pointing device can be used to sequentially touch each of the graphical electrode representations 26' corresponding to the electrodes 26 to be linked, while a key on the keyboard (e.g., shift key) can be continuously depressed. This is especially an efficient technique to employ when the electrodes 26 to be linked are not immediately adjacent to each other.

Figure 8E:
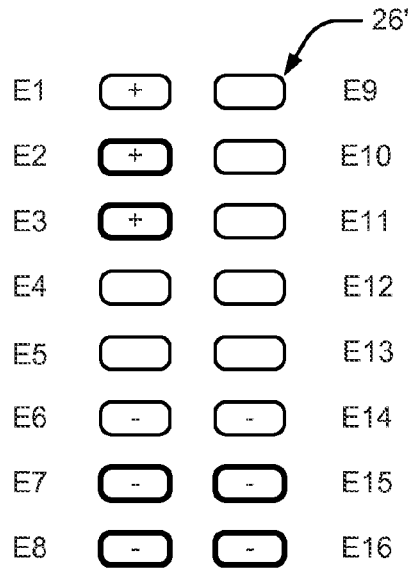

In any event, after all of the electrode subsets are defined, any of the electrode representations 26', including those associated with the defined electrode subsets, can be actuated (touched or clicked) to toggle the electrode between an off-state and an on-state (with the on-state having two polarizations that can be toggled in the case of a multipolar electrode arrangement, and the on-state having only one polarization in the case of a monopolar electrode arrangement). In the case where an electrode subset is actuated, each of the electrodes in the subset will have the same off-state/on-state when any one of the electrodes in the subset is selected and assigned that state. For example, as illustrated in FIG. 8E, electrodes E2, E3, E7, E8, E15, and E16 have been assigned an on-state, with the electrodes E2 and E3 being configured as anodes (+) (by specifically selecting either of these electrodes and toggling it to an anode (+)), and electrodes E7, E8, E15, and E16 being configured as cathodes (−) (by specifically selecting any of these electrodes and toggling it to a cathode (−)). Of course, any of electrodes E2, E3, E7, E8, E15, and E16 can be assigned back to an off-state by specifically selecting and toggling any of the electrodes. Electrode E1 has also been individually configured as an anode (+), and electrodes E6 and E14 have also been individually configured as cathodes (−).

Figure 8F:
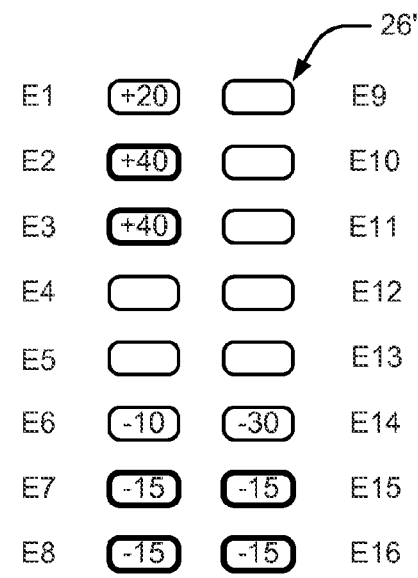

The current adjustment control 114 can be repeatedly actuated to independently increase or decrease the fractionalized current for the selected electrode 26 or electrodes 26 (in the case of a selected electrode subset). For example, as illustrated in FIG. 8F, electrode E1 has been individually assigned a fractionalized anodic current value of 20%, and electrodes E2 and E3 have been globally assigned a fractionalized anodic current value of 40% each. Electrode E6 has been individually assigned a fractionalized cathodic current value of 10%, electrode E14 has been individually assigned a fractionalized cathodic current value of 30%, and electrodes E7, E8, E15, and E16 have been globally assigned a fractionalized cathodic current value of 15% each.

Figure 8G:
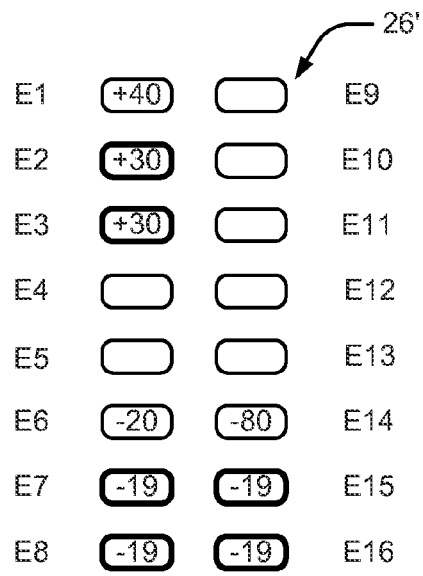

As illustrated in FIG. 8G, the fractionalized anodic current for electrode E1 has been individually modified to have a value of 40%, and the fractionalized anodic current for electrodes E2 and E3 have been globally modified to have a value of 30% each. Because 100% of the anodic current must be conserved, these modifications can be performed by selecting electrode E1 and increasing its fractionalized anodic current, or by selecting one of the electrodes E2 and E3 and decreasing its fractionalized anodic current. As also illustrated in FIG. 8G, the fractionalized anodic current for electrode E6 has been individually modified to have a value of 14%, the fractionalized anodic current for electrode E14 has been individually modified to have a value of 10%, and the fractionalized anodic current for electrodes E7, E8, E15, and E16 have been globally modified to have a value of 19% each. Because 100% of the anodic current must be conserved, these modifications can be performed by selecting electrode E6 and decreasing its fractionalized anodic current.

Of course, as briefly discussed above, the on/off state and stimulation amplitude value for the electrodes in an electrode subset may be globally modified using a control (not shown) that may appear next to any electrode representation 26' associated with the electrode subset that has been touched or clicked, as described in U.S. patent application Ser. No. 13/200,629, which has been previously incorporated herein by reference, or a control that may be superimposed over the electrode representation 26' that has been touched or clicked, as described in U.S. Provisional Patent Application Ser. No. 61/486,141, which has been previously incorporated herein by reference, or by typing or writing into a graphical symbol associated with the electrode representation 26', as will be described in further detail below.

Also pertinent to the present inventions, the user interface of the CP 18 provides the ability to conveniently copy/cut a previously assigned stimulation parameter value (e.g., stimulation amplitude value or on/off state) from one electrode (or an electrode subset) to another electrode (or another electrode subset).

Thus, the stimulation parameter value previously assigned to one of the electrodes 26 or electrode subsets can be copied and/or cut from the one electrode or electrode subset and pasted to another one of the electrodes 26 or electrode subsets in any one of a variety of manners. For example, the controller/processor 80 may be configured for copying and/or cutting the stimulation parameter value previously assigned to one of the electrodes 26 or electrode subsets in response to selecting the graphical electrode representation 26' with the pointing device, as well as pasting the stimulation parameter value to the other electrode 26 or electrode subset. The electrode representations 26' may be presented as graphical representations adapted to be manipulated using a pointing device.

In some cases described below, the pointing device can be used to select, drag, and/or drop graphical electrode representations 26'. The manner in which the graphical electrode representation 26' is selected, dragged, and dropped will depend on the nature of the user interface.

For example, when employing a conventional display screen 76 in conjunction with a mouse 72 or other pointing device, the user may select the graphical electrode representation 26' by, e.g., placing the cursor over the graphical electrode representation and clicking or pressing the appropriate button of the mouse 72. The user can then move the cursor to drag the graphical electrode representation within the programming screen 100, thereby moving the graphical representation to a desired location on the display. Once the graphical electrode representation 26' positioned as desired, the user can release the mouse button, thereby dropping the graphical electrode representation 26' at the desired location.

Alternatively for a touchscreen, also known as a digitizer screen, a stylus or finger is used, and the user may select the graphical electrode representation 26' by, e.g., physically touching the screen where the graphical electrode representation 26' is located. The user can drag the graphical electrode representation 26' by moving the stylus/finger across the programming screen 100, finally dropping the electrode representation 26' at a desired location.

Figure 9A:
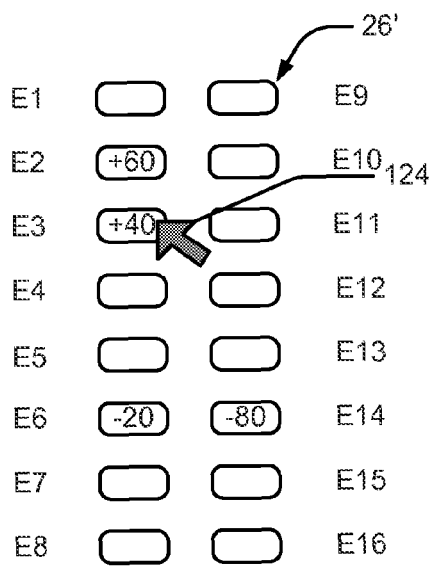
FIGS. 9A-9D are plan views respectively illustrating one technique used by the CP of FIG. 6 to copy/cut and paste a stimulation parameter value from one electrode to another electrode.
Figure 9B:
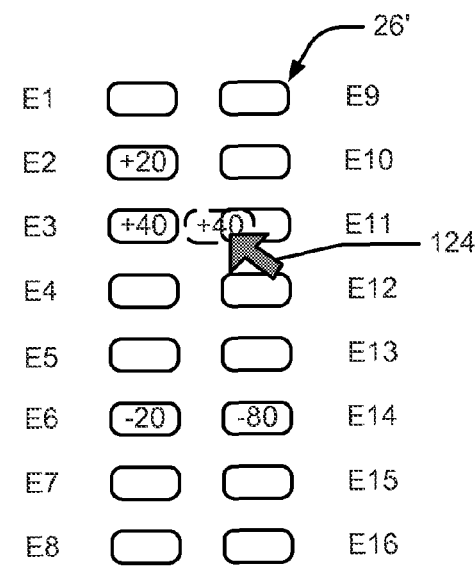
Figure 9C:
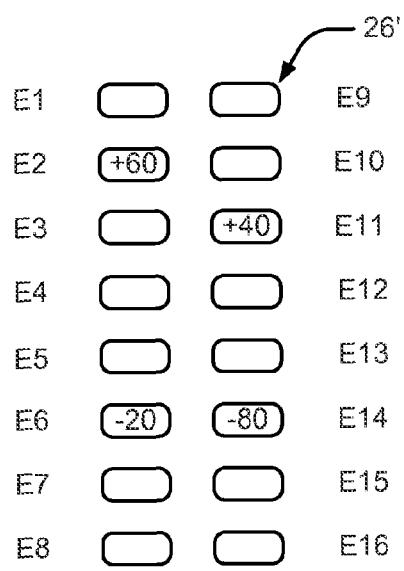
Figure 9D:
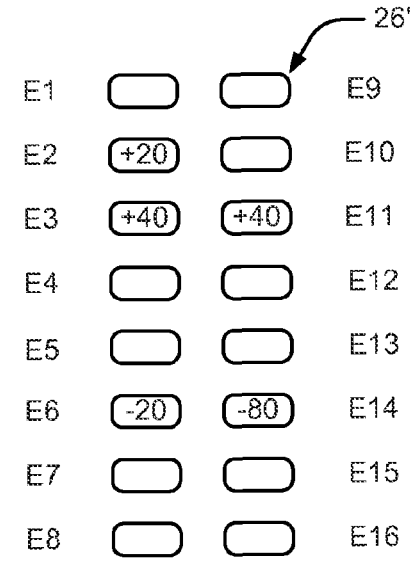

Referring to FIGS. 9A-9C, the graphical electrode representation 26' corresponding to electrode E3 can be selected by an actual or virtual pointing device 124 (in the illustrated case, a cursor) (FIG. 9A). The user can then drag that representation towards the graphical electrode representation 26' corresponding to electrode E11 (FIG. 9B), and then drop it into the graphical electrode representation 26' corresponding to electrode E11. That operation either copies or cuts the fractionalized anodic current value previously assigned to electrode E3 and pastes that value to electrode E11. The distinction between cutting and copying depends on the installed GUI and will be known to the operator. If the first value cut and pasted (that is, moved from electrode E3 to E11), the exact fractionalized anodic current value will be retained for electrode E11, as shown in FIG. 9C, and thus the total current remains unchanged. However, if the graphical electrode representation 26' is copied and pasted, as shown in FIG. 9D, then the total current does change, and an adjustment to electrodes E2-E4 must be made to conserve 100% of the total anodic current. Modifications to the fractionalized current values may be performed in accordance with a Ratio Maintenance Rule (RMR) described in further detail below. The process of cutting/copying and pasting can be repeated to change fractionalized anodic current values, one electrode at a time.

Figures 10A, 10B:
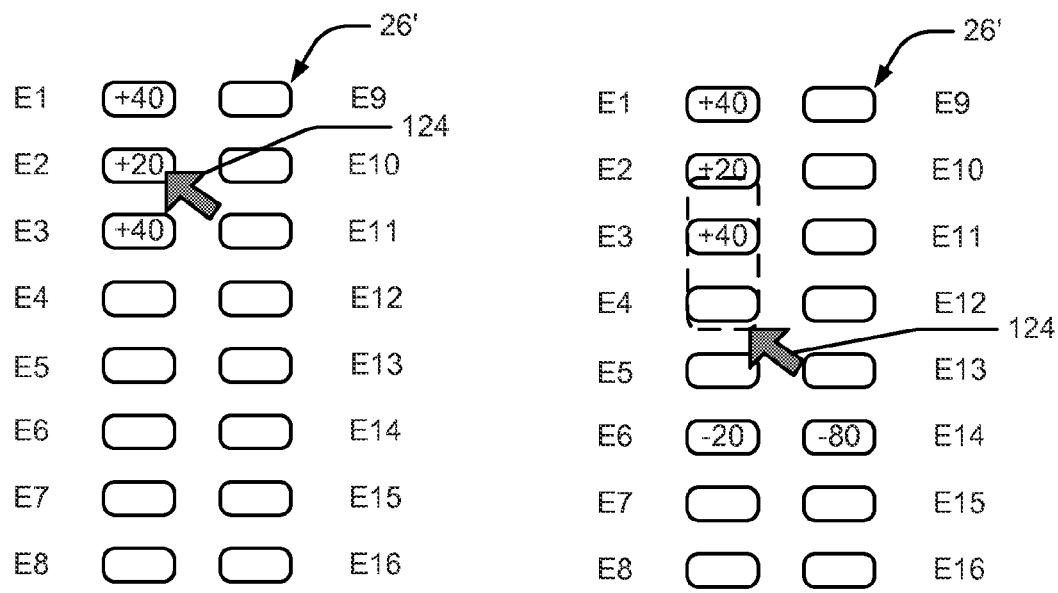
FIGS. 10A-10C are plan views respectively illustrating another technique used by the CP of FIG. 6 to copy/cut and paste a stimulation parameter value from one electrode to another electrode.
Figure 10C:
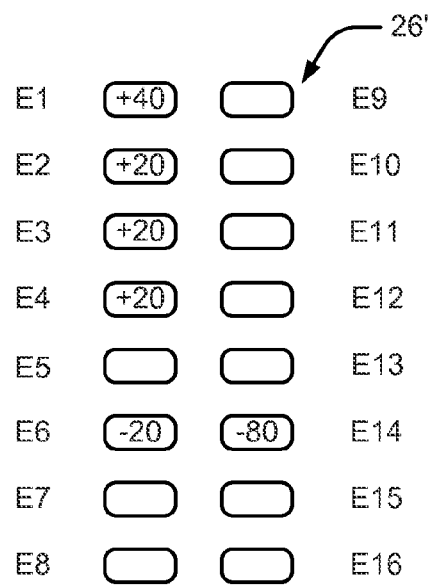

Turning to FIGS. 10A-10C, in another example the edge of the graphical electrode representation 26' corresponding to electrode E2 can be selected by an actual or virtual pointing device 124 (in the illustrated case, a cursor) (FIG. 10A), dragged to include the graphical electrode representations 26' corresponding to electrodes E3 and E4 (FIG. 10B), and released (FIG. 10C), thereby copying and pasting the fractionalized anodic current value previously assigned to electrode E2 to electrodes E3 and E4. Again, an adjustment to electrodes E1-E4 must be made to conserve 100% of the total anodic current. For example, the fractionalized anodic current for electrodes E2-E4 can be equalized, effectively decreasing the fractionalized anodic current for electrode E2. Again, modifications to the fractionalized current values may be performed in accordance with a RMR described in further detail below. In this manner, the fractionalized current value can be copied/cut and pasted to multiple electrodes at one time.

In the further example shown in FIGS. 11A-11D, the graphical electrode representation 26' corresponding to electrode E2 can be selected by an actual or virtual pointing device 124 (in the illustrated case, a cursor) to display a menu 128, a copy or cut command can be selected from the menu 128 (FIG. 11A), the graphical electrode representation 26' corresponding to electrode E10 can be selected by the cursor 124 to display the menu 128, and a paste command can be selected from the menu 128 (FIG. 11B), thereby copying/cutting and pasting the fractionalized anodic current value previously assigned to electrode E2 to electrode E10. If the graphical electrode representation 26' is cut and pasted, the exact fractionalized anodic current value will be retained for electrode E10 (FIG. 11C). However, if the graphical electrode representation 26' is copied and pasted, an adjustment to electrodes E2, E3, and E10 must be made to conserve 100% of the total anodic current (FIG. 11D). Modifications to the fractionalized current values may be performed in accordance with the RMR described in further detail below.

Although examples have been described for copying/cutting and pasting stimulation parameter values between different electrodes that have not been linked together, it should be appreciated that the same copying/cutting and pasting techniques can be used to copy/cut and paste stimulation parameter values between different linked electrode subsets. Furthermore, although examples have been described for copying/cutting and pasting stimulation amplitude value, other types of stimulation parameter values (e.g., an on/off state including polarity) can be copied/cut and pasted.

Also pertinent to the present inventions, the user interface of the CP 18 provides the user the ability to directly assign a stimulation parameter value (e.g. stimulation amplitude value or on/off state) to an electrode.

It can be seen that the various methods of assigning stimulation parameter values in the embodiments set out above have all proceeded indirectly. That is, the user selects a parameter value for a particular electrode E1-E16 at one location, such as, for example, electrode specific current adjustment control 114 (FIG. 7). That control provides a convenient location and process for inputting values, but the user is limited to incremental changes (that is, values are altered by pressing the appropriate arrow and waiting for the control 114 to step through all intermediate values).

Some embodiments may allow the user to assign a new stimulation parameter value, such as, for example, a new stimulation amplitude value, by directly entering a desired value by typing with a key board, or writing with a stylus, or other input device.

Referring to FIGS. 12A-12C, each electrode representation 26' includes a data box, which may contain a parameter value. A user may select a given electrode by clicking on an electrode representation 26' with cursor 124 for a conventional display or by touching that area on a touchscreen, as shown in FIG. 12A. That selection activates a data box 130, as shown in FIG. 12B. The user can then directly enter a parameter value, employing a suitable input device, such as a keyboard to enter a stimulation parameter value, thereby assigning a new stimulation parameter value to the selected graphical electrode representation 26', as shown in FIG. 12C. Deselecting the electrode representation 26' saves the entered value to memory 66. A number of alternative methods can be employed to effect the direct entry described herein. For example, the display need not set out a data box for each electrode representation 26'; rather, selecting an electrode representation could open a pop-up window or dialog box containing one or more data boxes, into which the user can enter the desired data.

Referring to FIGS. 13A-13C, the user can also directly enter data into a touchscreen, also known as a digitized display device. Here, a given electrode representation 26' can be selected by tapping or touching a particular electrode representation by a stylus 132 (or a finger). A pop-up window 134 may serve as an alternative to the data box 130 shown in FIGS. 12A-12C. The user can then use the stylus 132 to enter parameter data. Deselecting, by tapping somewhere else on the screen or by tapping on a close button 136 on the window 134 (FIG. 13B) may close the window 134 and save the entered value to memory 66. Alternatively, deselecting, by tapping somewhere else on the screen or by tapping on the close button 136 on the window 134 will cancel the current entered parameter data and revert back to the previously entered parameter data. In an alternate embodiment, the touchscreen may include a virtual keyboard to enter parameter data.

The data directly entered according to the embodiments shown in FIGS. 12A-13C can relate to either absolute electrical current amplitude values or to fractionalized electrical current values. These parameter values are explained in detail above. Where fractionalized current values are employed any changes require further adjustment to remaining electrodes 26 in order to conserve the total distributed current at 100%. Modifications to the fractionalized current values may be performed in accordance with the RMR as described in further detail below.

The RMR is a method of conserving fractionalized current values so that the sum of all fractionalized distributions equals 100%. Clearly, if the value of a target electrode is changed, the remaining electrodes having the same polarity as the target electrode (the "adjustment set") must be altered in response. To apply the RMR to a given set of electrodes, one first determines the "Original Ratio"—the ratio of each electrode's fractionalized current value to the total fractionalized current value of the adjustment set. Then, a "New Total" value is calculated as the changed fractionalized current value of the target electrode subtracted from 100. The new value of each electrode in the adjustment set is then calculated as the product of that electrode's Original Ratio and the New Total. That formula is explained and illustrated below.

Implementing the RMR may be accomplished in any one of a variety of manners. For example, the controller/processor 80 may be configured to modify the fractionalized current value of each electrode 26 (the electrodes may or may not have any previously assigned values) in response to the user's changes in the fractionalized current value of a target electrode, as discussed. For example, a user can assign a new fractionalized current value to an electrode 26, and afterward the CP 18 can follow one of the following algorithms to modify the fractionalized current values of the other electrodes 26.

Referring to FIGS. 14A-14C, one embodiment of the present invention applies an algorithm, referred to here as the Online Adjustment Mode ("ONAM"). That process follows the RMR described above, as follows. Consider an implementation having a total fractionalized cathodic current of −100, distributed to electrodes E1, E5, and E6, having fractionalized current values of −40, −20, and −40 respectively (FIG. 14A). (This means that if, for example, the absolute total cathodic current is −20 mA, then its fractionalized current value is −100, and the electrodes E1, E5, and E6 receive 40% of −20 mA=−8 mA, 20% of −20 mA=−4 mA, and 40% of −20 mA=−8 mA respectively.) Here, if the user selects electrode E1 (FIG. 14B) as the target electrode, leaving the adjustment set as electrodes E5 and E6. Thus, the Original Ratio for each electrode within the adjustment set may be calculated as follows:

Original Ratio of $E5=E5/(E5+E6)=$
 $-20/(-20+(-40))=\frac{1}{3}$

Original Ratio of $E6=E6/(E5+E6)=$
 $-40/(-20+(-40))=\frac{2}{3}$

Thus, E5 receives ⅓ of the current available for distribution to the adjustment set and E6 distributes ⅔ of that current.

The user then assigns E1 a new value of −10. Upon that assignment, the CP 18 updates the fractionalized current values according to the RMR, employing the ONAM algorithm. Here, the New Total current available for distribution to the adjustment set is a fractionalized current value of −90.

New Total=−100−New value of $E1=-100-(-10)=-90$.

The updated fractionalized current values of the adjustment set electrodes E5 and E6 can be calculated as follows:

$E5$=Original Ratio of $E5 \times$New Total=⅓×(−90)=−30

$E6$=Original Ratio of $E6 \times$New Total=⅔×(−90)=−60

It should be noted that the ONAM operates on the fly, adjusting fractionalized current values each time the user changes the value of a target electrode. Thus, the CP 18 here assigns the calculated fractionalized current values to the adjustment set electrodes E5 and E6 according to their cathodic polarity: E5=−30 and E6=−60 (FIG. 14C).

In an alternate algorithm, referred to as the Offline Adjustment Mode ("OFAM"), the total set, comprising the target electrode together with the adjustment set electrodes, is not updated automatically but rather the update routine is initiated in an auto-adjust command issued by the user, through an action such as pressing a button, entering a keyboard shortcut, tapping the touchscreen, etc. The new fractionalized value of an electrode E can be given as the ratio of E within the new total set including the target electrode multiplied by 100.

Two points distinguish the OFAM process with that of the ONAM. First, the OFAM treats the entire set of electrodes having the same polarity as the adjustment set. Thus, in calculating ratios, the target electrode is not treated differently from other electrodes. Second, the fact that the OFAM operates on command, rather than automatically, allows multiple electrodes to be assigned new values.

Referring to the example shown in FIGS. 15A-15C, three electrodes, E1, E5, E6 distribute 100% of the cathodic current, having fractionalized current values of −40, −20, and −40, respectively (FIG. 15A). Here the user selects the electrode E1 as the target electrode, and assigns E1 a new value −20 (FIG. 15B). Upon initiation from the user, the CP 18 updates the fractionalized current values of the electrode set according to the RMR using the OFAM algorithm. The updated fractionalized current values of the adjustment set electrodes 26 can be calculated as follows:

$$E1 = E1/(E1+E5+E6) \times 100 = 20/(20+20+40) \times 100 = 25$$

$$E5 = E5/(E1+E5+E6) \times 100 = 20/(20+20+40) \times 100 = 25$$

$$E6 = E1/(E1+E5+E6) \times 100 = 40/(20+20+40) \times (100-10) = 50$$

It can be noted here that electrode E1 was assigned a new value of 20, but after application of the RMR that value was altered to 25. Polarity can be assigned after the calculations are performed, producing assignments of −25, −25, and −50, respectively (FIG. 15C). Although, the examples provided above use a fractionalized current value, absolute current amplitudes can be used for applying RMR using ONAM and OFAM. In this case, assuming that a total current amplitude of all electrodes of the same polarization must be maintained, the absolute current amplitude values assigned to the electrodes can be transformed into fractionalized current values by dividing the absolute current amplitude values by the total current amplitude, applying the RMR to the fractionalized current values to obtain new fractionalized current values, and then transforming the new fractionalized current values back to absolute current values.

Also pertinent to the present inventions, the software of the CP 18 provides several additional features such as program rule checking, adjusted value display, and a locking mechanism.

With respect to the program rule checking feature, the CP 18 may evaluate the values assigned to the electrodes based on a number of program rules criteria. For example, a program rule could specify a maximum allowable bandwidth, or maximum allowable energy, or the like. Actions resulting from violation of such rules can similarly be set out in the program. A condition lying outside specified criteria, for example, could initiate feedback in the form of a visual or audio indicator, such as a pop-up window or audible alarm. Software routines for implementing such actions are well known in the art.

With respect to the adjusted value display feature, the CP 18 displays the final current values for all electrodes in a convenient location and format as each target electrode value is entered by the user. The location can be anywhere on the screen 100, or on an external display device. For the ONAM, the values displayed can be for all non-target electrodes 26, and the values can be accepted when the user completes entry for the target electrodes 26. For the OFAM, the values displayed can be for all the electrodes 26, and the values displayed can be accepted as soon as the user triggers the adjustment routine.

With respect to locking mechanism feature, the CP 18 may link a set of the electrodes 26 together in response to the actuation of a control element on the user interface, and further prevents the current values assigned to this linked set of electrodes from being varied relative to each other, as described in U.S. Provisional Patent Application Ser. No. 61/561,760, entitled "Techniques for Linking Electrodes Together during Programming of Neurostimulator System," which application is incorporated herein in its entirety. For example, if a current value is assigned to a target electrode 26 in response to a user input, any adjustment of non-target electrodes 26 that are linked to the target electrode 26 will be varied in proportion to the current value assigned to the target electrode 26. In effect, any electrodes 26 linked to the target electrode 26 become target electrodes themselves. Alternatively, the CP 18 prevents the current values assigned to the linked set of electrodes from being varied at all, in effect, locking the linked set of electrodes.

Although the foregoing techniques have been described as being implemented in the CP 18, it should be noted that this technique may be alternatively or additionally implemented in the RC 16. Furthermore, although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for use with a neurostimulator coupled to a plurality of electrodes capable of conveying electrical stimulation energy into tissue in which the electrodes are implanted, comprising:
    a user interface configured for receiving:
        an activation selection from a user to select a subset of the plurality of electrodes as activation electrodes to be activated as either cathodes or anodes for conveying the electrical stimulation energy into tissue;
        a first input from a user manually selecting a smaller subset of two or more of the electrodes having the same polarity to be linked for specifying at least one of a stimulation amplitude value and an on/off state for each electrode in the smaller subset of the electrodes; and
        a second input from the user manually specifying a single entry to be assigned to each of the electrodes in the smaller subset of electrodes, wherein the single entry includes a stimulation amplitude value or an on/off state, the user interface including a display screen configured for displaying graphical representations of the electrodes;
    a controller/processor configured for, in response to the first input from the user, linking the smaller subset of electrodes together, and in response to the second input from the user specifying the single entry, assigning the stimulation amplitude value or the on/off state only to each of the electrodes in the smaller subset of the electrodes; and
    output circuitry configured for transmitting the at least one of the stimulation amplitude value and on/off state to the neurostimulator.

2. The external control device of claim 1, wherein the single entry comprises the stimulation amplitude value.

3. The external control device of claim 2, wherein the stimulation amplitude value is a fractionalized amplitude value.

4. The external control device of claim 2, wherein the display screen is configured for displaying a stimulation amplitude adjustment control, and the second user input comprises repeatedly actuating the stimulation amplitude adjustment control to incrementally increase or decrease the stimulation amplitude value.

5. The external control device of claim 2, wherein the display screen is configured for displaying a graphical data entry symbol, and the second user input comprises writing or typing the stimulation amplitude value into the graphical data entry symbol.

6. The external control device of claim 1, wherein the single entry comprises the on/off state.

7. The external control device of claim 6, wherein the on/off state comprises the polarity.

8. The external control device of claim 6, wherein the display screen is configured for displaying an on/off state adjustment control, and the second user input comprises actuating the on/off adjustment control to change the on/off state.

9. The external control device of claim 1, wherein the first user input comprises using a pointing device.

10. The external control device of claim 9, wherein the first user input comprises using the pointing device to draw a border that encompasses the graphical electrode representations corresponding to the smaller subset of the electrodes.

11. The external control device of claim 9, wherein the first user input comprises using the pointing device to individually select the graphical electrode representations corresponding to the smaller subset of the electrodes.

12. The external control device of claim 1, wherein the user interface is configured for receiving a third input from the user, and wherein the controller/processor is further configured for, in response to the third input from the user, duplicating the at least one of the stimulation amplitude value and on/off state previously assigned to the electrodes of the smaller subset of the electrodes to electrodes of a different smaller subset of the electrodes.

13. The external control device of claim 12, wherein the controller/processor is configured for cutting/copying and pasting the at least one of the stimulation amplitude value and on/off state previously assigned to the electrodes of the smaller subset of the electrodes to the electrodes of the different smaller subset of the electrodes.

14. The external control device of claim 1, further comprising a housing containing the user interface, controller/processor, and output circuitry.

15. An external control device for use with a neurostimulator coupled to a plurality of electrodes capable of conveying electrical stimulation energy into tissue in which the electrodes are implanted, comprising:
a user interface configured for receiving:
  a selection of a subset of the plurality of electrodes to be activated as either cathodes or anodes for conveying the electrical stimulation energy into tissue;
  a selection of a smaller subset of two or more of the electrodes to be linked together for assigning a value of a stimulation parameter to each of the electrodes in the smaller subset of electrodes; and
  a single entry specifying the value of the stimulation parameter to be assigned to each of the electrodes in the smaller subset of electrodes, the user interface including a display screen configured for displaying graphical representations of the electrodes;
a controller/processor configured for linking the smaller subset of electrodes together and assigning the value of the stimulation parameter to each of the electrodes in the smaller subset of the electrodes; and
output circuitry configured for transmitting the value of the stimulation parameter to the neurostimulator.

16. The external device of claim 15, wherein the value of the stimulation parameter includes a stimulation amplitude value.

17. The external device of claim 15, wherein the value of the stimulation parameter includes an on/off state.

18. The external control device of claim 15, wherein the user interface is configured to receive the selection of the smaller subset of the electrodes by receiving a drawn border that encompasses the graphical electrode representations corresponding to the smaller subset of the electrodes.

19. The external control device of claim 15, wherein the user interface is configured to receive the selection of the smaller subset of the electrodes by receiving individual selections of the graphical electrode representations corresponding to the smaller subset of the electrodes.

20. The external control device of claim 15, wherein user interface is configured for displaying a stimulation amplitude adjustment control on the display screen, and the user interface is configured to receive the single entry specifying the value of the stimulation parameter by actuating the stimulation amplitude adjustment control to incrementally increase or decrease the stimulation amplitude value.

* * * * *